United States Patent
Dreyfuss

(10) Patent No.: US 8,430,909 B2
(45) Date of Patent: *Apr. 30, 2013

(54) KNOTLESS GRAFT FIXATION USING AN IMPLANT HAVING A POINTED TIP

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/182,893

(22) Filed: Jul. 14, 2011

(65) Prior Publication Data

US 2011/0276092 A1  Nov. 10, 2011

Related U.S. Application Data

(63) Continuation of application No. 12/022,868, filed on Jan. 30, 2008, now Pat. No. 7,993,369, which is a continuation-in-part of application No. 10/045,707, filed on Apr. 3, 2003, now Pat. No. 7,329,272, which is a continuation-in-part of application No. 09/886,280, filed on Jun. 22, 2001, now Pat. No. 6,544,281.

(60) Provisional application No. 60/213,263, filed on Jun. 22, 2000.

(51) Int. Cl.
  *A61B 17/04* (2006.01)
  *A61B 17/56* (2006.01)

(52) U.S. Cl.
  USPC ........... 606/232; 606/139; 606/144; 606/104; 606/73

(58) Field of Classification Search .................. 606/139, 606/144, 104, 73, 232, 75
  See application file for complete search history.

(56) References Cited

U.S. PATENT DOCUMENTS

| 5,002,550 A | 3/1991 | Li |
| 5,152,790 A * | 10/1992 | Rosenberg et al. ........ 623/13.14 |

(Continued)

FOREIGN PATENT DOCUMENTS

WO  WO 99/37217 A1  7/1999

OTHER PUBLICATIONS

Arthrex, Inc., "PushLock SP," screenprints, pp. 1/8 to 8/8 and animation, Oct. 15, 2007. http://www.arthrex.com/resources/animation/sjjiLfkEEeCRTQBQVoRHOw/pushlock-sp.

(Continued)

*Primary Examiner* — Vy Q. Bui
(74) *Attorney, Agent, or Firm* — Dickstein Shapiro LLP

(57) ABSTRACT

A method for securing soft tissue to bone which does not require the surgeon to tie suture knots to secure the tissue to the bone. Suture is passed through the graft at desired points. A cannulated plug or screw is pre-loaded onto the distal end of a driver provided with an eyelet implant at its distal end. Suture attached to the graft is passed through the eyelet of the implant located at the distal end of the driver. The distal end of the driver together with the eyelet implant is inserted into the bone. Tension is applied to the suture to position the graft at the desired location relative to the bone. The screw or plug is advanced into the pilot hole by turning the interference screw or tapping the plug until the cannulated screw or plug securely engages and locks in the eyelet implant, so that the cannulated plug or screw with the engaged eyelet implant is flush with the bone. Once the screw or plug is fully inserted and the suture is impacted into the bone, the driver is removed and any loose ends of the sutures protruding from the anchor site are then clipped short.

8 Claims, 12 Drawing Sheets

U.S. PATENT DOCUMENTS

| | | |
|---|---|---|
| 5,643,320 A * | 7/1997 | Lower et al. ............... 606/232 |
| 6,280,474 B1 * | 8/2001 | Cassidy et al. ............ 623/16.11 |
| 6,544,281 B2 | 4/2003 | ElAttrache et al. |
| 7,083,638 B2 | 8/2006 | Foerster |
| 7,993,369 B2 * | 8/2011 | Dreyfuss ................... 606/232 |
| 2004/0093031 A1 | 5/2004 | Burkhart et al. |
| 2005/0277986 A1 | 12/2005 | Foerster et al. |
| 2006/0004364 A1 | 1/2006 | Green et al. |
| 2006/0100630 A1 | 5/2006 | West |
| 2007/0191849 A1 | 8/2007 | ElAttrache et al. |
| 2007/0225719 A1 | 9/2007 | Stone et al. |

OTHER PUBLICATIONS

Wikipedia, Wikipedia "Osseointegration" http://en.wikipedia.org/wiki/Osseonintegration.

* cited by examiner

KNOTLESS GRAFT FIXATION USING AN IMPLANT HAVING A POINTED TIP

This is a continuation of U.S. application Ser. No. 12/022,868, filed Jan. 30, 2008, now U.S. Pat. No. 7,993,369, which is a continuation-in-part of U.S. application Ser. No. 10/405,707, filed Apr. 3, 2003, now U.S. Pat. No. 7,329,272, which is a continuation-in-part of U.S. application Ser. No. 09/886,280, filed Jun. 22, 2001, now U.S. Pat. No. 6,544,281, which claims the benefit of U.S. Provisional Application Serial No. 60/213,263, filed Jun. 22, 2000.

FIELD OF THE INVENTION

The present invention relates to methods and instruments for fixation of sutures and tissue to bone.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Various fixation devices, including sutures, screws, staples, wedges, and plugs have been used in the past to secure soft tissue to bone. For example, in typical interference screw fixation, the graft is fixed to the bone by driving the screw into a blind hole or a tunnel in the bone while trapping the end of the graft between the screw and the bone tunnel. In other methods, the graft is simply pinned against the bone using staples or sutures tied around the end of the graft to the bone.

Application Ser. No. 09/886,280 filed on Jun. 22, 2001, the disclosure of which is incorporated by reference herein, discloses a surgical technique and associated instruments for securing soft tissue to bone which does not require the surgeon to tie suture knots to secure the tissue to the bone. According to the technique, a cannulated plug or screw is pre-loaded onto the distal end of a cannulated driver, and a suture or wire loop is passed through the cannula of the driver so that a looped end of the suture or wire is exposed at the distal end of the driver. Suture strands attached to a graft are fed through the loop at the end of the driver, and the driver is inserted into the bottom of the hole, with the screw or plug disposed just outside the hole. With tension applied to the suture or wire loop to keep the graft at the desired location relative to the bone hole, the screw or plug is then fully advanced into the hole using the driver to frictionally secure either the suture attached to the graft or the graft itself into the bone hole.

Although the above-described technique provides an improved method of graft fixation to bone, the flexible loop configuration at the end of the driver disadvantageously impedes sliding of the suture or graft which is fed through the suture loop. In addition, because the cannulated driver of application Ser. No. 09/886,280 is provided with a flexible loop at its distal end, placement of the suture or graft at the bottom of the blind hole or socket and the cortical bone must be approximated, thus sometimes necessitating additional removal, tapping and insertion steps to ensure full insertion of the plug or screw into the blind hole or socket. This, in turn, may abrade the adjacent tissue and/or damage the bone or cartilage.

Accordingly, a need exists for an improved surgical technique and associated device for securing soft tissue to bone which allows the free sliding of the suture ends attached to a graft to ensure the positioning of the graft at an appropriate distance from the device. A fixation device and associated surgical technique that allow precise advancement and guiding of the plug or screw into the blind hole or socket are also needed.

SUMMARY OF THE INVENTION

The instruments and methods of the present invention overcome the disadvantages of the prior art, such as those noted above, by providing an eyelet implant at the distal end of a driver that securely engages and locks into a cannulated ribbed body of an interference plug or screw. The eyelet implant includes a fixed aperture for receiving a suture attached to a graft, such that the suture is able to freely slide through the aperture.

In one embodiment of the invention, suture is passed through the graft at desired points. A cannulated plug or screw is pre-loaded onto a driver provided with an eyelet implant at its distal end. Suture attached to the graft is passed through an aperture of the eyelet implant located at the distal end of the driver. The distal end of the driver together with the eyelet implant is inserted directly into the bone. The screw or plug is fully advanced into the pilot hole by tapping the interference screw or plug until the cannulated plug or screw securely engages and locks in the eyelet implant. Once the screw or plug is fully inserted and the suture is impacted into the bone, the driver is removed.

Other features and advantages of the invention will become apparent from the following description of the invention, which refers to the accompanying drawings.

DETAILED DESCRIPTION OF THE PREFERRED EMBODIMENT

Figure 1:
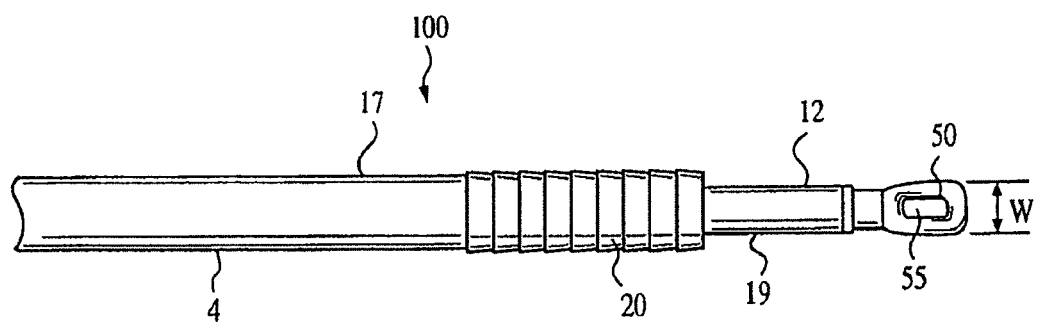
FIG. 1 illustrates a perspective view of a distal end of a push lock driver of the present invention.
Figure 2:
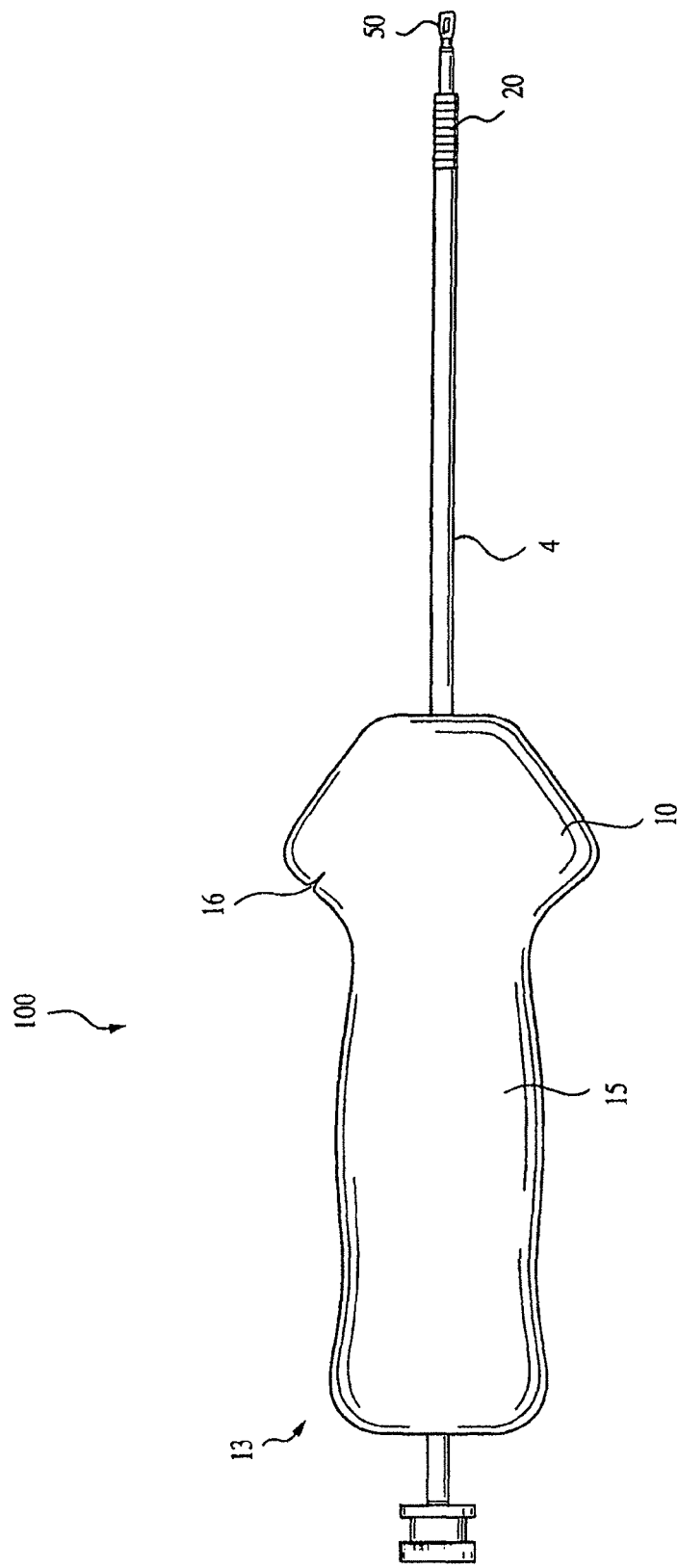
FIG. 2 illustrates a perspective view of a push lock driver of the present invention.

Referring now to the drawings, where like elements are designated by like reference numerals, FIGS. 1 and 2 illustrate an implant driver 100 of the present invention. Driver 100 includes a body 4, preferably in the form of a cylinder, and having a distal end 12 (FIG. 1) and a proximal end 13 (FIG. 2). The body 4 of driver 100 includes an outer shaft 17 and an inner shaft 19. The outer shaft 17 is cannulated for receiving inner shaft 19.

As illustrated in FIG. 1, driver 100 is pre-loaded with an interference device 20. Preferably, the interference device 20 is a screw or an interference plug, preferably formed of a bioabsorbable material such as PLLA. If a screw is employed, the screw may be provided with a cannulated body provided with a continuous thread having rounded outer edges. The head of the screw may be rounded to minimize abrasion or cutting of tissue. The cannulation formed through the screw is preferably hex-shaped and accepts the correspondingly shaped inner shaft 19 of driver 100. If an interference plug is desired, the plug is provided with rounded annular ribs separated by rounded annular grooves. The outer diameter of the ribs and grooves is substantially constant. The plug tapers significantly toward the distal end. The plug also comprises a cannula, preferably hex-shaped, for accommodating the inner correspondingly shaped shaft 19 of the corresponding driver 100.

As also shown in FIG. 1, an eyelet implant 50 is provided at the distal end 12 of driver 100. The eyelet implant 50 is releasably attached to the distal end 12 of driver 100 by means of a connector 57. The eyelet implant 50 is formed of a transparent polymer material, and is preferably made of a bioabsorbable material such as PLLA, polyglycolic or polylactic acid polymers. Advantageously, the eyelet implant 50 is made of a material similar to that of the interference device 20. As illustrated in FIG. 1, the eyelet implant 50 is provided with aperture 55 for receiving a suture attached to a graft to pass through the eyelet implant 50, as described in more detail below. The width "w" (FIG. 1) of the eyelet implant 50 is about equal the diameter of the inner shaft 19 and slightly smaller than the diameter of the outer shaft 17 and of the cannula of the interference device 20.

FIG. 2 illustrates proximal end 13 of driver 100, showing a handle 15 disposed coaxially with the body 4 and outer shaft 17 and provided with handle slots or protuberances 16. As described below, handle slots or protuberances 16 allow a suture strand to be wrapped around the handle 15 and be subsequently tensioned prior to the impaction of the interference device 20 into the pilot hole. In this manner, the graft is precisely positioned at an appropriate distance from the pilot hole, and the suture with the attached graft is secured at the bottom of the pilot hole and prevented from exiting the pilot hole.

Figure 3:
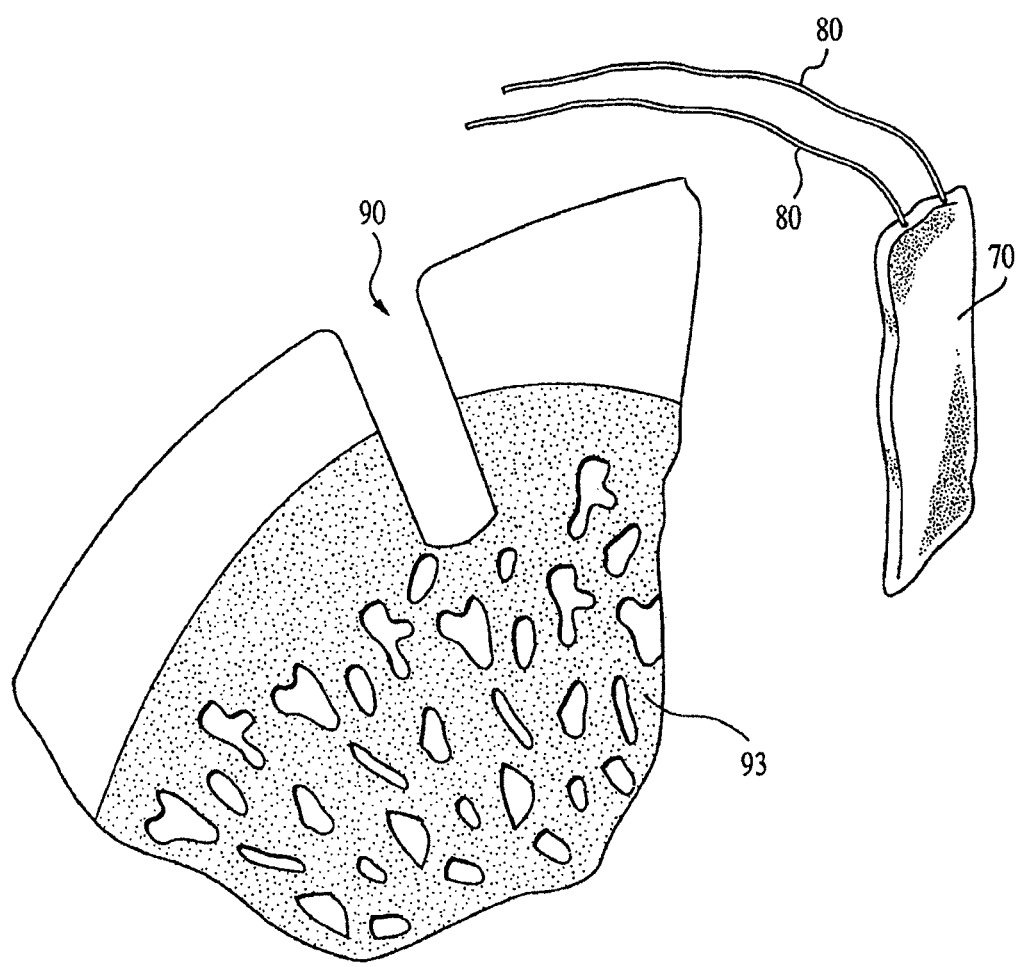
FIG. 3 is a schematic cross-sectional view of a surgical site undergoing a graft fixation technique according to a method of the present invention.

A method of a graft fixation technique according to the present invention is now described with reference to FIGS. 3-8. The present invention may be used to secure any type of soft tissue, graft, or tendon, such as, for example, a biceps tendon or a rotator cuff. FIG. 3 illustrates at least one suture 80 passed though the graft 70 at desired points. FIG. 3 also illustrates a pilot hole or socket 90 formed in the bone or cartilage 93 using a drill or punch, at the location where the tissue is to be secured. A punch provides the advantages of rounding the opening edge of the bone socket to protect the sutures 80 attached to the graft 70 from being sheared during the insertion process, and also compacts the bone at the punch site for better attachment of the bone by the anchor in cases where the bone is a soft bone.

Figure 4:
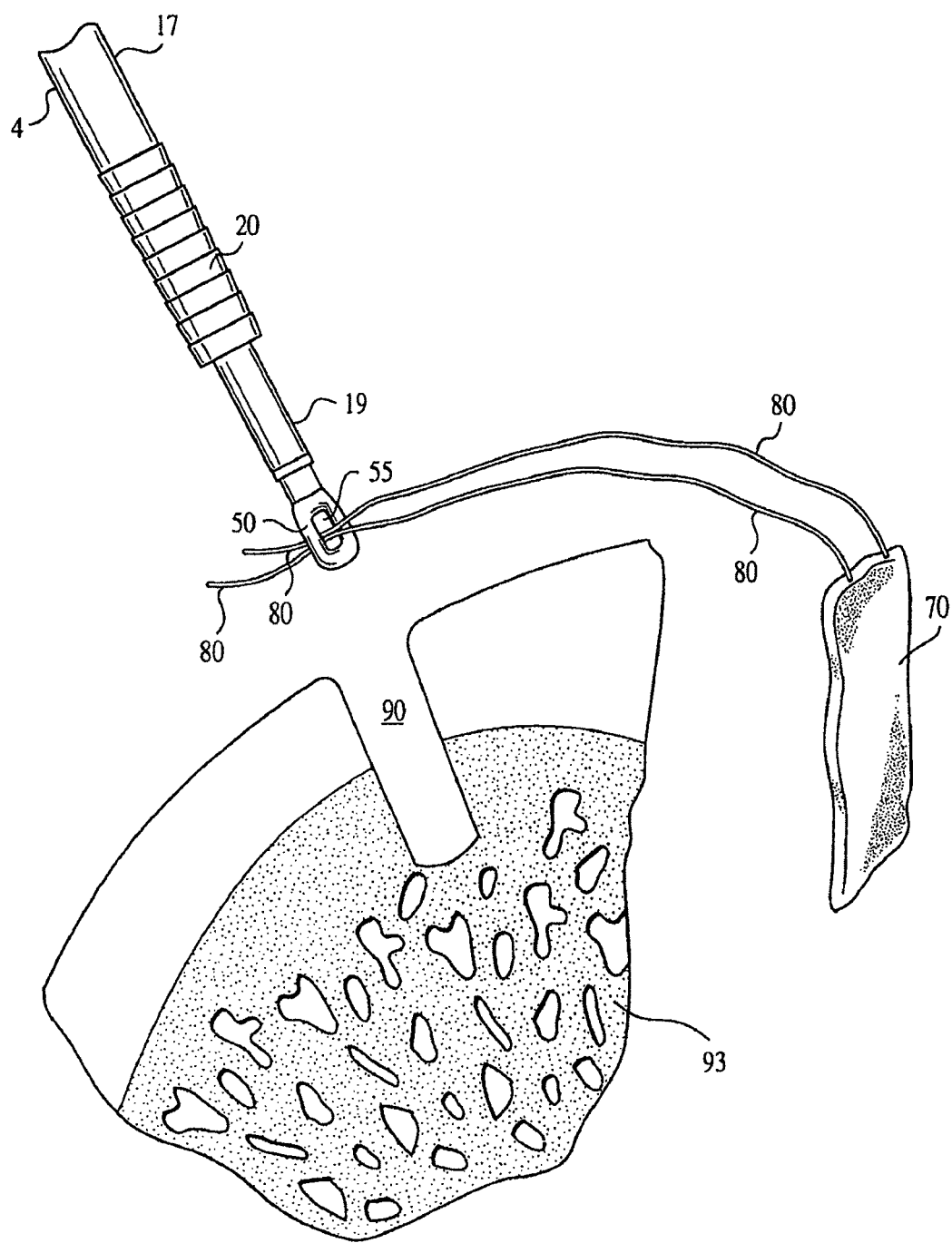
FIG. 4 is a schematic view of the surgical site of FIG. 3 undergoing a graft fixation technique with the push lock driver of FIGS. 1-2.

Next, as shown in FIG. 4, driver 100 with a pre-loaded interference device 20 and with the outer shaft 17 in the retracted position is provided in the proximity of the bone socket 90. Sutures 80 attached to the graft 70 are subsequently passed through the aperture 55 of the eyelet implant 50 at the end of driver 100, as shown in FIG. 4.

Figure 5:
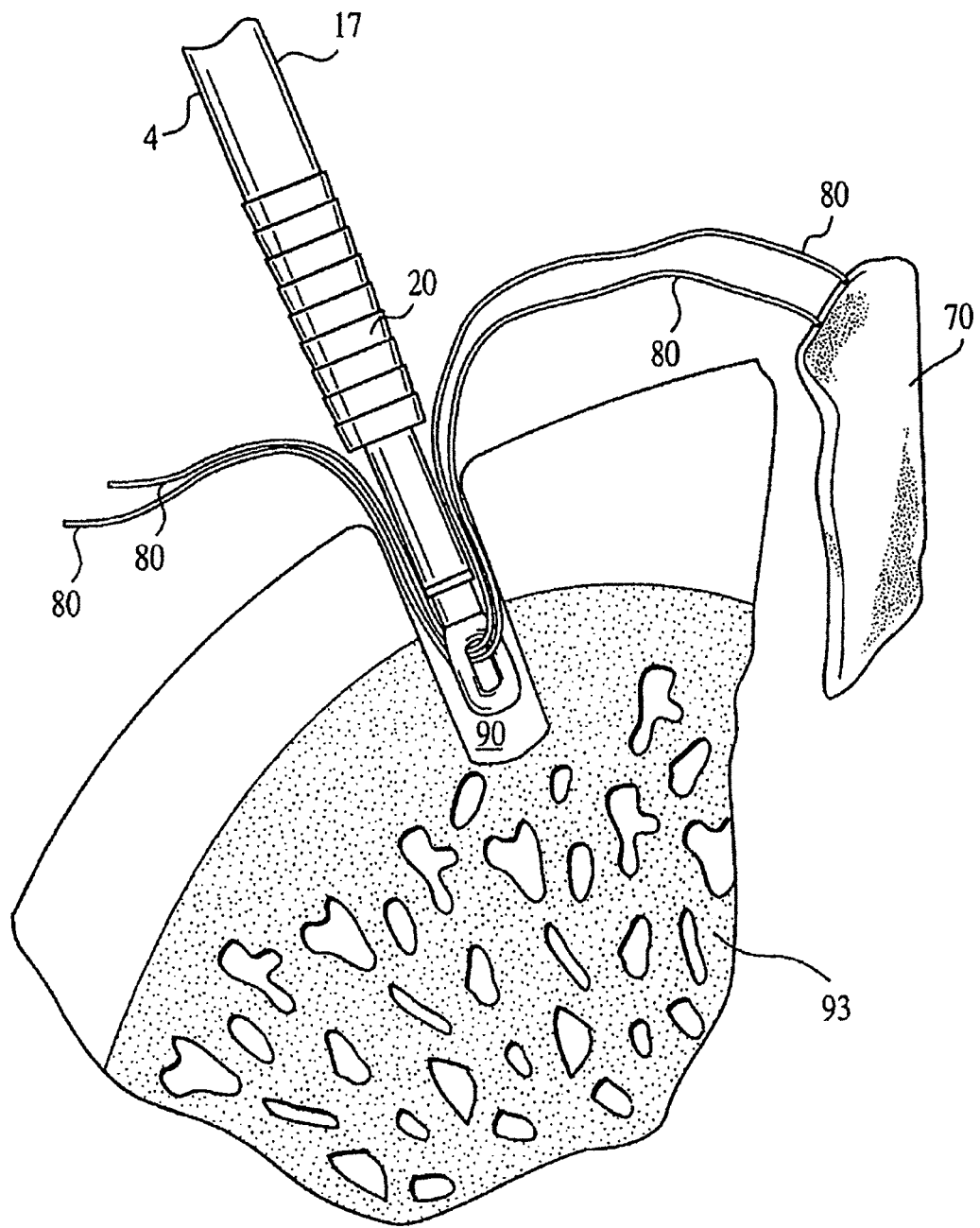
FIG. 5 is a schematic view of the surgical site of FIG. 3 undergoing a graft fixation technique with the push lock driver of FIGS. 1-2 and at a stage subsequent to that shown in FIG. 4.
Figure 6:
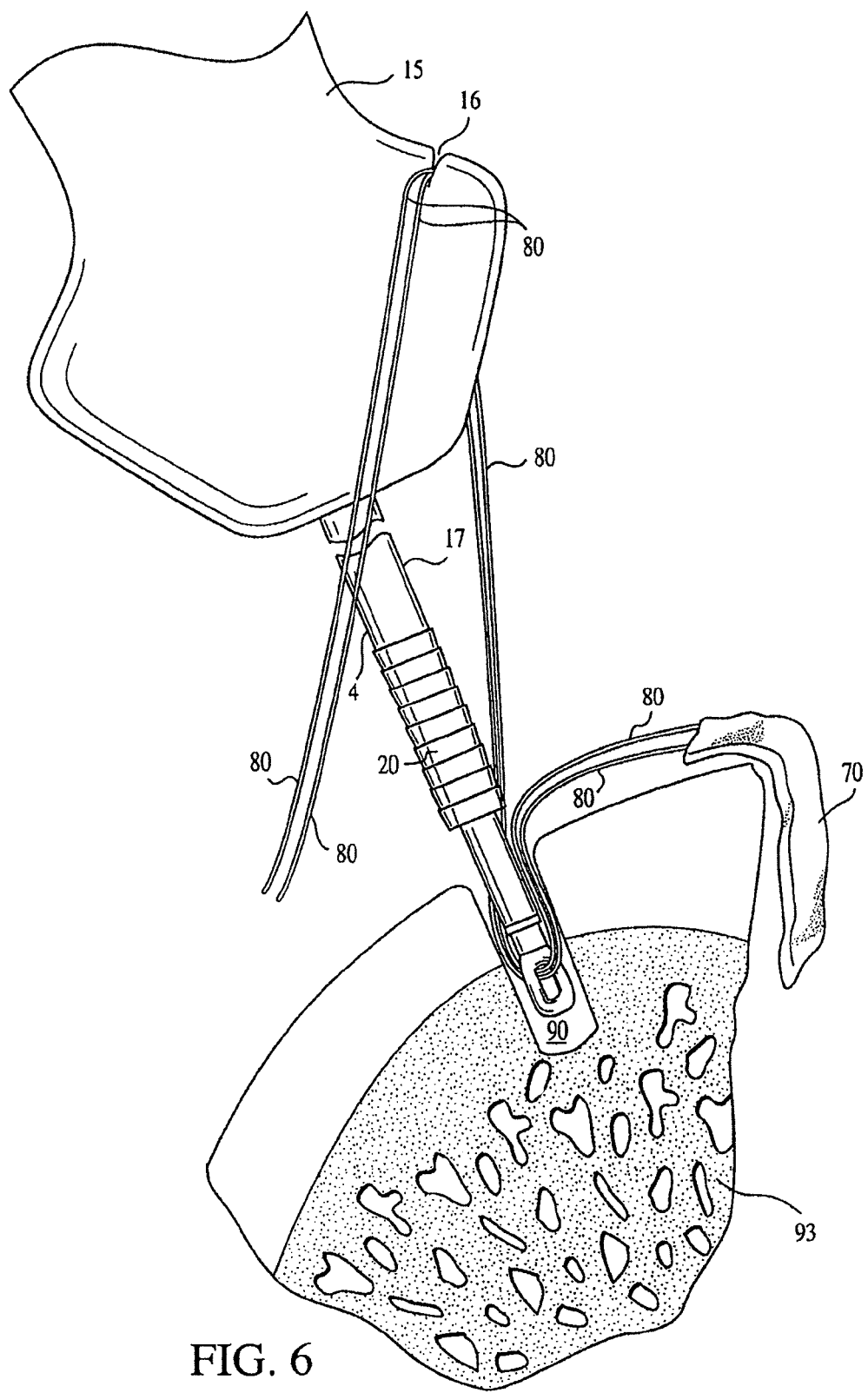
FIG. 6 is a schematic view of the surgical site of FIG. 3 undergoing a graft fixation technique with the push lock driver of FIGS. 1-2 and at a stage subsequent to that shown in FIG. 5.
Figure 7:
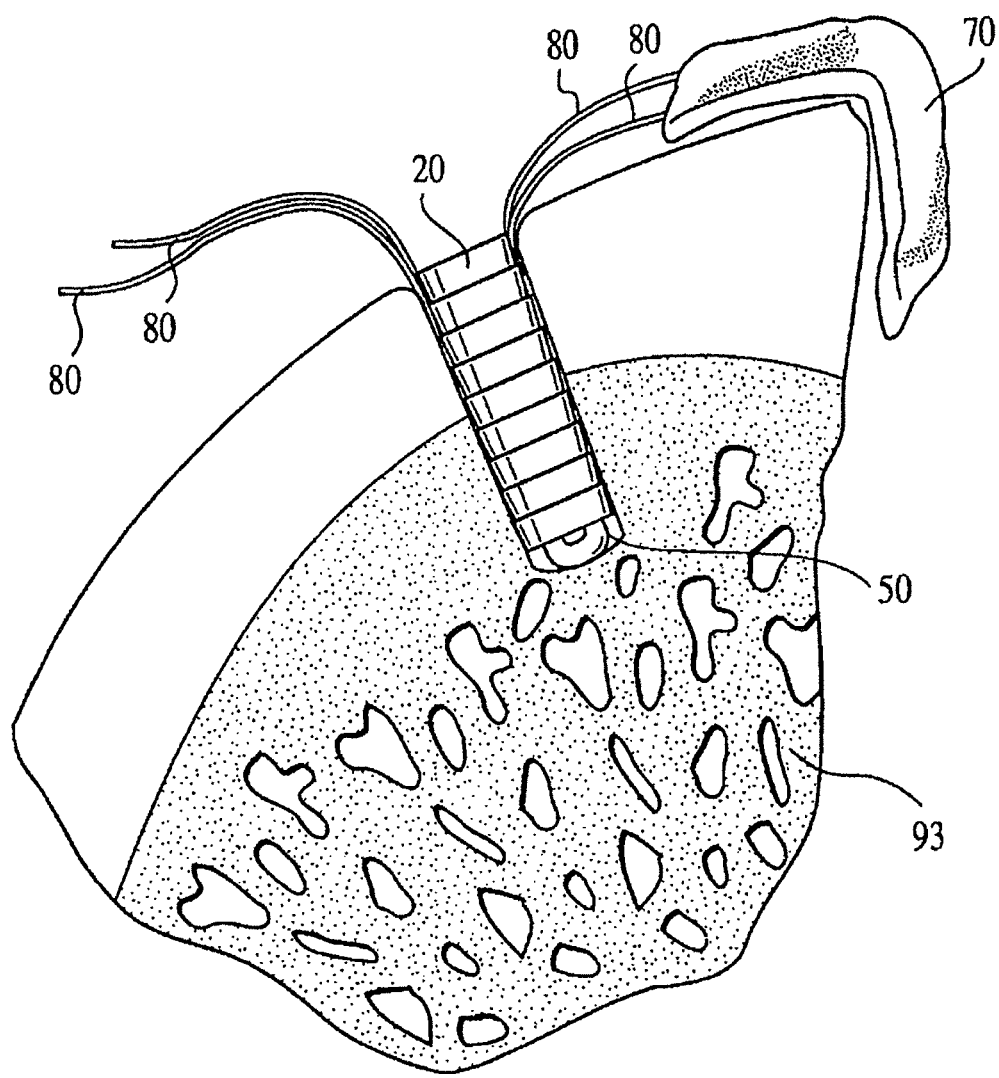
FIG. 7 is a schematic view of the surgical site of FIG. 3 undergoing a graft fixation technique with the push lock driver of FIGS. 1-2 and at a stage subsequent to that shown in FIG. 6.
Figure 8:
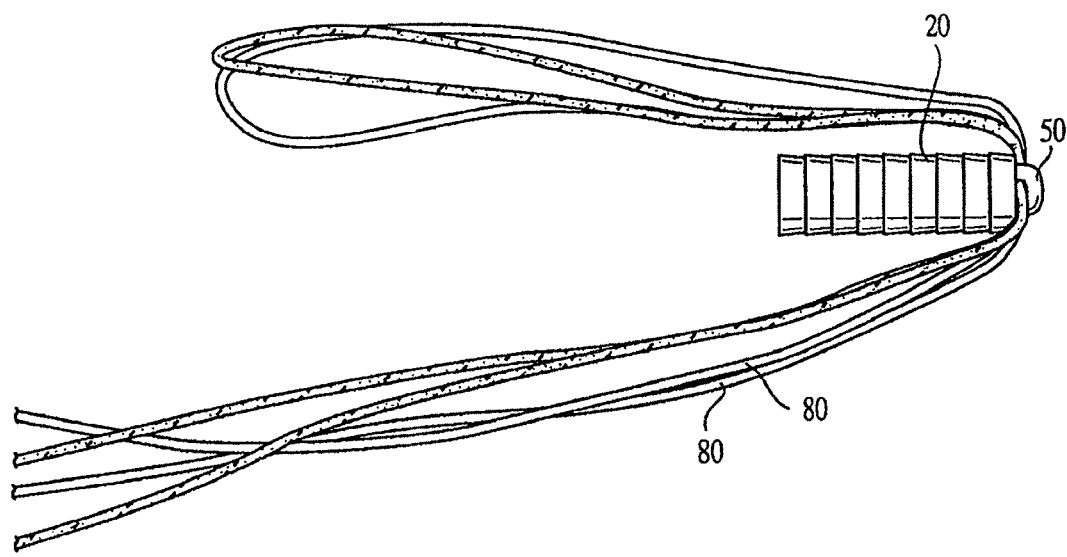
FIG. 8 is a schematic view of an eyelet implant of the present invention secured by and locked into an interference device, and in accordance with an embodiment of the present invention.

Referring now to FIG. 5, driver 100 is held with gentle pressure so that the eyelet implant 50 at the distal end 12 is held at the bottom of the hole 90, keeping the interference device 20 just outside the pilot hole 90. Tension is then applied to the suture 80 by wrapping the suture 80 around the slots 16 of the handle 15 and tensioning it, as shown in FIGS. 6-7. The suture 80 freely slides through aperture 55 of the eyelet implant 50, allowing the graft 70 to be positioned close to the edge of the pilot hole 90. Once tensioning of the suture 80 has been completed, the interference device 20 is then impacted into the pilot hole 90 so that the interference device 20 advances toward the distal end 12 of driver 100 and securely engages and locks in the eyelet implant 50 with the sutures 80, as shown in FIGS. 7-8. After the interference device 20 is fully inserted, the driver is removed and the ends of the sutures can be removed by clipping them short, leaving the graft 70 securely fastened to bone 93.

A significant advantage of the present invention is that the sutures attached to the graft or the graft itself can be securely attached to the bone without the need to tie knots. Additionally, the suture attached to the graft is secured both by the eyelet implant and by the interference device, along the bottom and sidewalls of the pilot hole between the bone and the screw or plug, conferring a much stronger fixation of the graft to the bone than is achievable with prior art procedures and devices. More importantly, the suture attached to the graft is allowed to freely slide through the aperture of the eyelet implant to allow precise advancement and guiding of the plug or screw into the blind hole or socket.

Figure 9:
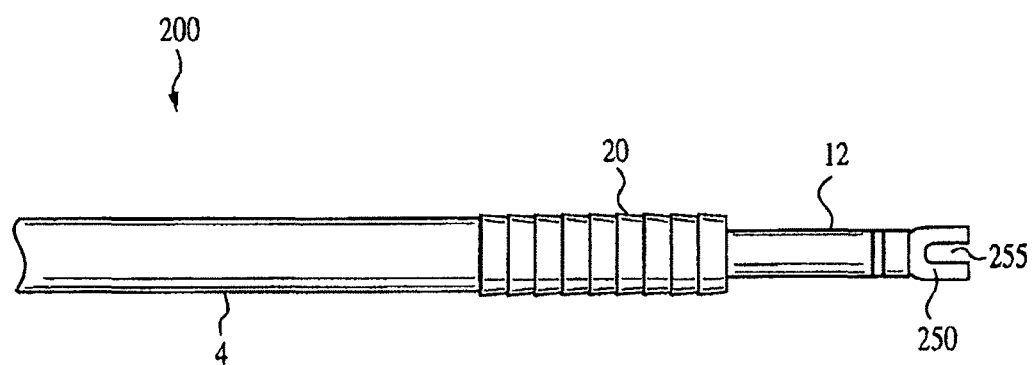
FIG. 9 illustrates a perspective view of a distal end of a push lock driver in accordance with a second embodiment of the present invention.

In another embodiment of the present invention illustrated in FIG. 9, driver 200 is provided with a horseshoe-shaped implant 250 (i.e., an implant with an open distal end) at the distal end of the driver in lieu of the eyelet implant. The horseshoe-shaped implant 250 is provided in the form of a wedge 255 that allows the suture attached to a graft to be securely contained within the wedge, yet be capable to freely slide within the wedge. The horseshoe-shaped implant 250 is formed of a transparent polymer material, and is preferably made of a bioabsorbable material such as PLLA, polyglycolic or polylactic acid polymers. Advantageously, the horseshoe-shaped implant 250 is made of a material similar to that of the interference device 20.

The horseshoe-shaped implant 250 may be detachable from the distal end 12 of the driver 200, similar to the eyelet implant described in detail above. In this embodiment, the detachable horseshoe-shaped implant 250 is securely engaged within the cannulated ribbed body of the interference plug or screw 20. Alternatively, the horseshoe-shaped implant 250 may be integral with the distal end 12 of the driver 200 and, after the interference screw or plug 20 is fully inserted into the pilot hole, the horseshoe-shaped implant 250 is removed from the site together with the driver 200.

Figure 10:
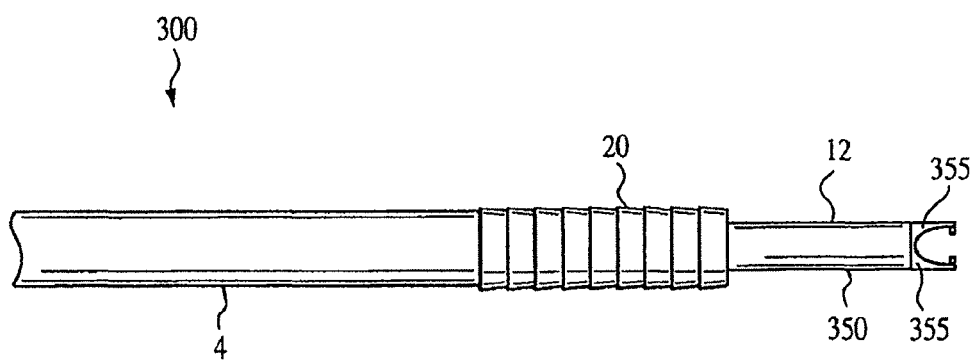
FIG. 10 illustrates a perspective view of a distal end of a push lock driver in accordance with a third embodiment of the present invention.

In yet another embodiment of the present invention and as illustrated in FIG. 10, driver 300 of the present invention is provided with a metal tubing 350 at the distal end of a driver, which in turn, is provided with a cut or pair of protuberances 355 at its most distal end to allow at least one end of a suture attached to a graft to be securely contained within the cut, yet be capable to freely slide within the cut. Preferably, the metal tubing 350 is integral with the distal end 12 of the driver 300 and, subsequent to the full insertion of the interference screw or plug 20 into the pilot hole, the metal tubing 350 is removed from the site together with the driver 300.

FIGS. 11-15 illustrate another embodiment of the present invention, according to which driver 400 is provided with a pointed tip implant 450 at the distal end of the driver, which is also an eyelet implant but which, because of its pointed tip, does not require the pre-drilling or pre-formation of a hole for fixating the device (implant with suture attached to graft) in the bone. The conical configuration of the most distal end of the pointed tip implant 450 allows the driver 400 with the attached implant to undergo a self-punching operation during graft fixation, eliminating any need to pre-drill a hole in the bone and providing increased fixation of the overall operation of securing the soft tissue. The conical configuration of the most distal end of the pointed tip implant 450 also provides suture fixation strength, as well as accelerated graft/tendon healing to bone. The pointed tip implant 450 may be detachable from the driver.

Figure 11:
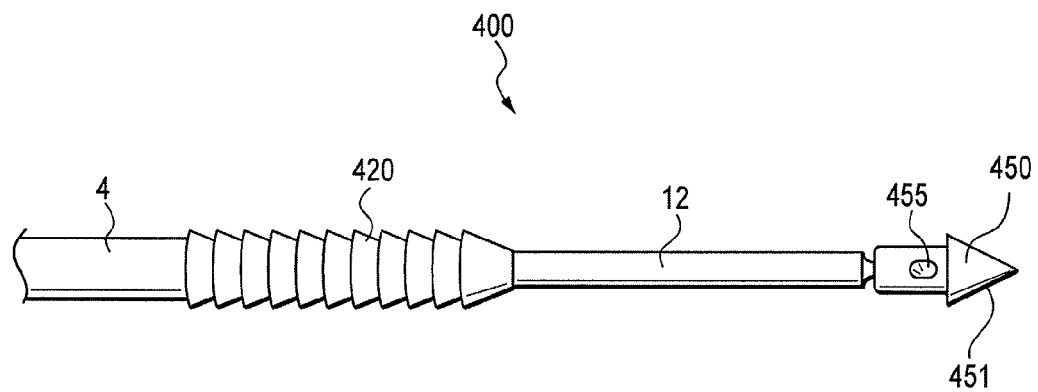
FIG. 11 illustrates a perspective view of a distal end of a push lock driver in accordance with a fourth embodiment of the present invention.
Figure 12:
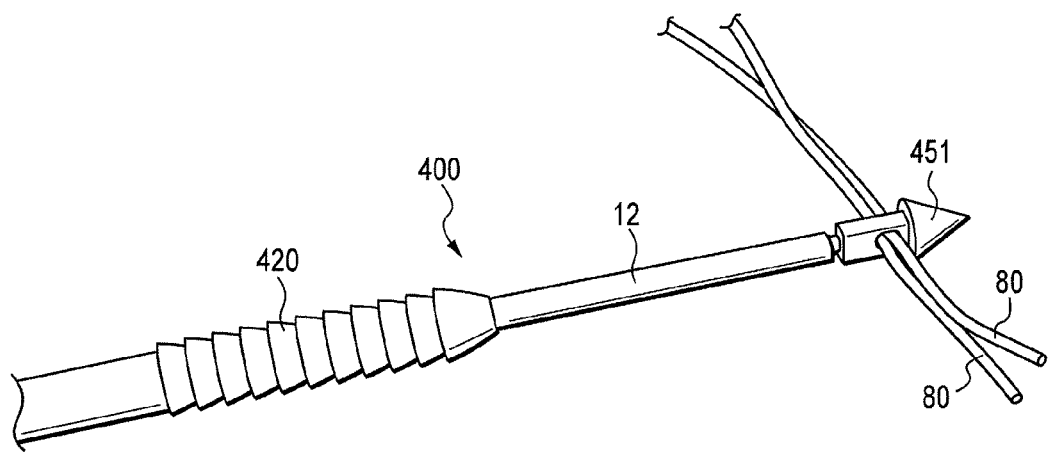
FIG. 12 illustrates another perspective view of the push lock driver of FIG. 11 with a strand passed through an aperture of the push lock.

As illustrated in FIGS. 11 and 12, pointed tip implant 450 is provided with an eyelet or aperture 455 for receiving at least one strand (for example, a suture strand) attached to a graft to pass through the eyelet implant 450. Pointed tip implant 450 is also provided, at its most distal end, with a conical portion 451 which allows direct advancement of the implant (by simply tapping the device with a mallet, for example) without the formation of a bone hole. Preferably, the conical portion 451 of the implant is formed of titanium or titanium alloy. In a preferred embodiment, eyelet or aperture 455 is also formed of titanium or similar material, to withstand impaction forces during the graft fixation procedure.

As in the previously-described first embodiment, strand 80 (attached to graft 70) is passed through the aperture 455 of the implant 450 at the end of the driver 400, as shown in FIGS. 11 and 12. Although FIG. 12 illustrate two strands 80 (i.e., two suture strands 80) passed through the aperture 455, the invention is not limited to this exemplary embodiment and contemplates additional embodiments wherein one strand or any number of strands are passed through the aperture 455. Preferably, at least one of the strands is formed of a high strength suture material such as FiberWire® suture, sold by Arthrex, Inc. of Naples, Fla., and described in U.S. Pat. No. 6,716,234, the disclosure of which is incorporated by reference herein. The high strength suture may be available in various lengths and widths. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. The suture may optionally include filaments of various colors.

Figure 14:
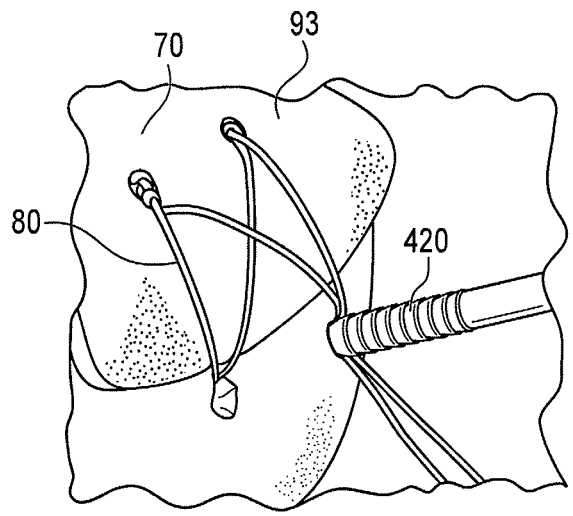
FIGS. 14 and 14A are schematic views of the surgical site of FIG. 13 at a graft fixation stage subsequent to that shown in FIG. 13.
Figure 15:
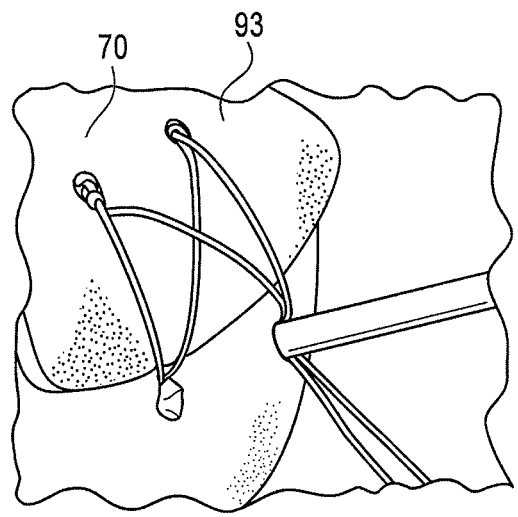
FIGS. 15 and 15A are schematic views of the surgical site of FIG. 13 at a graft fixation stage subsequent to that shown in FIGS. 14 and14A.

An exemplary method of graft fixation using the pointed tip implant 450 of the present invention is illustrated with reference to FIGS. 13-15. This exemplary method illustrated in FIGS. 13-15 relates to a specific graft fixation technique (i.e., SutureBridge Lateral Row fixation); however, the invention is not limited to this exemplary embodiment and applies to any other method of soft tissue fixation known in the art.

Figure 13:
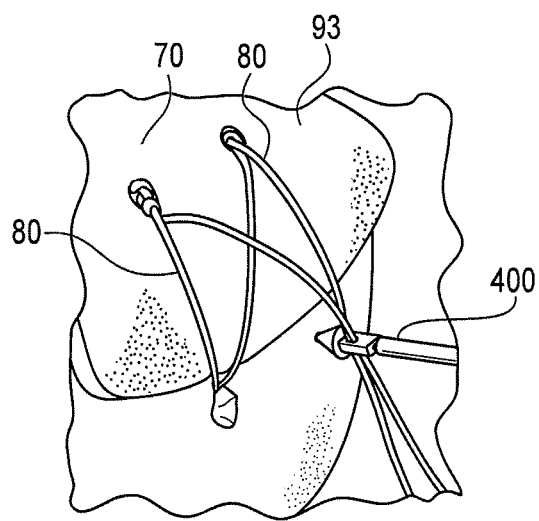
FIG. 13 is a schematic cross-sectional view of a surgical site undergoing a graft fixation technique with the push lock driver of FIGS. 11 and 12.
Figure 14A:
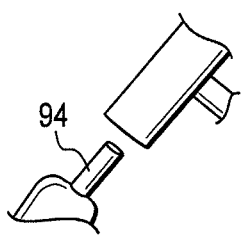
Figure 15A:
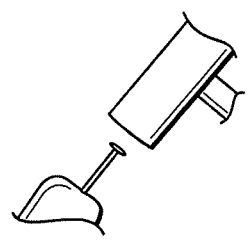

Referring to FIG. 13, an Arthrex SutureBridge® medial row is completed as known in the art and the strands 80 (suture strands 80) are threaded through the titanium eyelet 455. As shown in FIG. 14A, a protective cap 94 (or other device that prevents anchor deployment) is malleted to advance the PushLock° until the anchor contacts bone 93. The suture is then tensioned, as shown in FIG. 14. The protective cap 94 is subsequently removed (FIG. 15A) and the button 420 is malleted until mark (for example, a predefined laser line) is flush with the bone (FIG. 15). The ribbed, spiked configuration of plug or button 420 facilitates the insertion of the device 400 into the bone by simply exerting force upon the device, without the need to drill or form a hole in the bone.

Although the above embodiments have been described with reference to an implant, such as eyelet implant 50, 450 (FIGS. 1 and 11) or horseshoe-shaped implant 250 (FIG. 9), for example, having an aperture of a predefined configuration (i.e., eyelet or horseshoe configuration), it should be understood that the invention is not limited to these embodiments. Accordingly, the present invention also contemplates implants affixed to or detachable from a preloaded driver and having an aperture of any configuration or geometrical shape, as long as it captures suture and allows the captured suture to freely slide within the aperture.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of soft tissue repair, comprising the steps of:
    attaching at least one suture to a soft tissue graft to be affixed to a bone;
    capturing the suture attached to the graft by passing the suture through an aperture of an implant releasably attached at a distal end of a driver such that the suture can slide freely through the aperture of the implant, the implant having a conical portion terminating in a pointed tip at its most distal end;
    inserting the implant having a pointed tip and the suture passing through the implant into the bone using the driver, without pre-drilling a hole in the bone;
    pulling on one end of the suture to draw the suture through the aperture of the implant such that the soft tissue graft attached to the suture is drawn toward the bone; and
    advancing an interference device, preloaded on the driver, toward the distal end of the driver to securely engage and lock the implant and the suture in the bone.

2. The method of soft tissue repair according to claim 1, wherein the interference device is a screw.

3. The method of soft tissue repair according to claim 1, wherein the interference device is a plug.

4. The method of soft tissue repair according to claim 1, wherein the aperture has an eyelet configuration.

5. The method of soft tissue repair according to claim 1, wherein the implant is detachable from the distal end of the driver.

6. The method of soft tissue repair according to claim 1, wherein the implant comprises titanium or titanium alloy.

7. The method of soft tissue repair according to claim 1, wherein the suture is a high strength suture.

8. The method of soft tissue repair according to claim 1, wherein the driver includes an outer shaft disposed around an inner shaft and movable between a proximal position and a distal position along the inner shaft, and wherein the interference device is loaded onto the inner shaft by inserting the inner shaft through a cannula of the interference device with the outer shaft retracted to the proximal position so that the proximal end of the loaded interference device abuts the distal end of the outer shaft.

\* \* \* \* \*

UNITED STATES PATENT AND TRADEMARK OFFICE
CERTIFICATE OF CORRECTION

PATENT NO. : 8,430,909 B2 Page 1 of 1
APPLICATION NO. : 13/182893
DATED : April 30, 2013
INVENTOR(S) : Dreyfuss et al.

It is certified that error appears in the above-identified patent and that said Letters Patent is hereby corrected as shown below:

On the Title page, item (12), "Dreyfuss" should read --Dreyfuss et al.--

On the Title page, at item (75), as Inventors, add --Stephen S. Burkhart, San Antonio, TX (US) and Neal S. ElAttrache, Los Angeles, CA (US)--

Signed and Sealed this
Twenty-seventh Day of October, 2015

Michelle K. Lee
*Director of the United States Patent and Trademark Office*